US006761164B2

(12) United States Patent
Amirpour et al.

(10) Patent No.: US 6,761,164 B2
(45) Date of Patent: Jul. 13, 2004

(54) HERBAL VAPORIZER

(75) Inventors: Shahin Amirpour, 4909 River Ave., Newport Beach, CA (US) 92663; Justin Grissinger, Huntington Beach, CA (US)

(73) Assignee: Shahin Amirpour, Costa Mesa, CA (US)

( * ) Notice: Subject to any disclaimer, the term of this patent is extended or adjusted under 35 U.S.C. 154(b) by 78 days.

(21) Appl. No.: 10/156,779

(22) Filed: May 23, 2002

(65) Prior Publication Data

US 2003/0217750 A1 Nov. 27, 2003

(51) Int. Cl.$^7$ .............................................. A61M 16/00
(52) U.S. Cl. .................. 128/203.26; 261/DIG. 65; 239/136; 128/203.12; 392/386
(58) Field of Search .................. 392/386–391, 392/407, 410, 432–434; 96/361–364, 376; 261/DIG. 65; 131/194; 239/128, 135–139; 128/200.19, 200.24, 201.25, 202.21, 203.12, 203.23, 203.26, 203.27, 204.13, 203.25, 204.17, 205.27, 205.29, 207.14

(56) References Cited

U.S. PATENT DOCUMENTS

| 4,141,369 | A | * | 2/1979 | Burruss ....................... 131/330 |
| 6,095,153 | A | | 8/2000 | Kessler et al. |
| 6,250,301 | B1 | | 6/2001 | Pate |
| 6,513,524 | B1 | * | 2/2003 | Storz ..................... 128/203.26 |
| 2003/0075177 | A1 | * | 4/2003 | Balch et al. ........... 128/203.26 |

OTHER PUBLICATIONS

Air–2.com, "Better Living Through Technology," Excerpts from: www.air–2.com/vaporshop/store/about.asp. (Printed on Jun. 7, 2002). 4 pages.

Vapir.com, "Still Smoking?" Excerpts from: www.vapir.com. (Printed on Jun. 7, 2002). 6 pages.

Genuine Chills, "Genuine Chills Vapotron Vaporizers," Excerpts from: http://www.chillspipes.com, Chills pipes.com, (Printed on Mar. 19, 2002). 2 pages.

Marijuanavaporizer.com, "Home of the Marijuana Vaporizer", Excerpts from: http://www.marijuanavaporizer.com, Pure THC, (Printed on Mar. 20, 2002). 7 pages.

Herbalvaporizer.com, "Smoking Marijuana with the Herbal Vaporizer," Excerpts from: http://www.herbalvaporizer.com, Pure THC (Adelaide, Australia), (Printed on Mar. 20, 2002). 2 pages.

Vaporbrothers.com, "Welcome to Vapor Space 2002," Excerpts from: www.vaporbrothers.com, (Printed on Mar. 19, 2002). 16 pages.

* cited by examiner

Primary Examiner—Glenn K. Dawson
(74) Attorney, Agent, or Firm—Fulwider Patton Lee & Utecht, LLP

(57) ABSTRACT

A fire-resistant housing forming a heat generating compartment having an access opening and at least one elongated heating element which is coupled to a support element in said compartment to position a second end of the heating element proximate the access opening for vaporizing an herbal sample placed in close proximity thereof. Such second end is further positioned at a height equal to or less than the height between the first end and an underlying support surface. A connector is included to electrically connect the heating element to a power source for energizing the heating element.

16 Claims, 4 Drawing Sheets

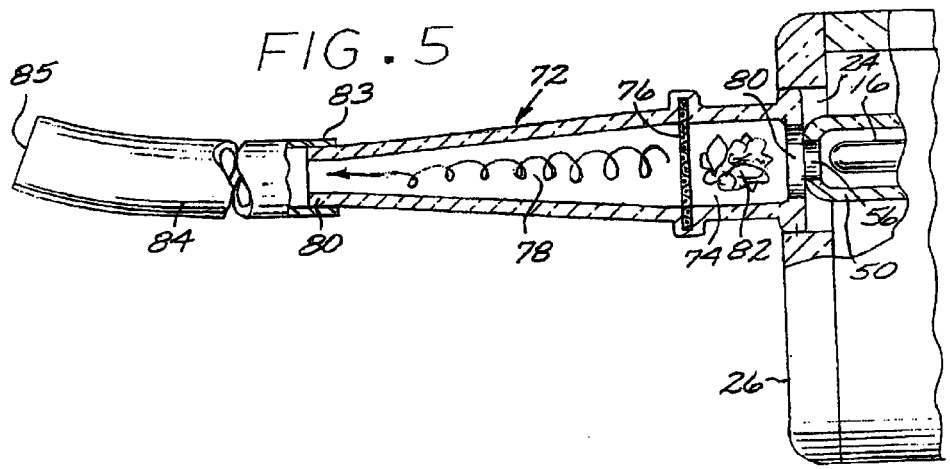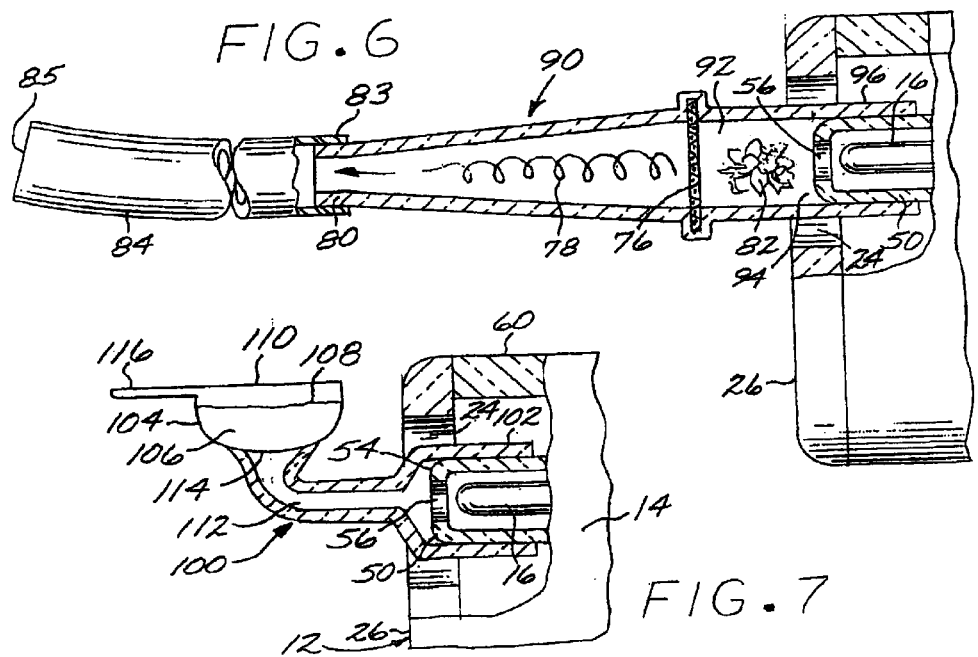

HERBAL VAPORIZER

BACKGROUND OF THE INVENTION

1. Field of the Invention

This invention relates generally to inhalation devices, and more specifically, to devices for extracting ingredients from a natural substance through vaporization.

2. Description of the Prior Art

The extraction of natural ingredients from naturally occurring substances such as botanicals has been found to have significant benefits both inside and outside the medical community. While the primary extraction method involves placing the product in a convenient form such as a pill to control the release rate and amount of the ingredients after ingestion, the benefits of directly inhaling the active ingredients into the circulatory system have desirable effects as well. Such inhalation methods circumvent the drawbacks associated with first digesting the product to process it into the bloodstream.

For this and other reasons, one common way of extracting the ingredients from a natural substance through inhalation is simply obtained from smoking the product by applying fire directly to the product, commonly contained in a paper wrapping of some sort, to burn the substance and inhale the desired ingredients as they are released. However, several disadvantages arise in light of inhaling undesirable particulate along with the desired ingredients. More specifically, smoke particles enter the user's throat and lungs, create an unpleasant burning smell, and introduce additional hazards into the user's body. Prolonged smoking introduces significant health risks in the mouth, throat, lungs and heart of the user. In addition, applying fire directly to the herbal product burns up a significant amount of the quantity resulting in using more than necessary to acquire the desired dosage and or effect.

Several devices which have reached the commercial marketplace seek to avoid the concerns caused by smoking the product. These devices seek to overcome the drawbacks of smoking by removing the smoke and carcinogens from the inhalation process as well as the odor caused by the smoke by vaporizing the product instead of burning it with flame applied directly to the herb. Some of these commercially available devices include a vapor collecting globe surrounding a platform upon which the desired quantity of an herb is placed. The plate is heated to vaporize the herbs until the globe is filled with a desired quantity of vapor. The vapors collected in the globe may be withdrawn by inhaling from a tube connected to a passage leading to the interior of the globe. However, as such devices require the user to place the herb directly on the heating plate, such construction introduces the potential burning disadvantages discussed above thereby introducing unwanted large particulate into the globe. The use of hot plate configuration also takes several minutes before the vapor is satisfactory. If the alternative method is used and the herb is packed directly into the heating element shaft, the vaporization process time is increased but so are the chances of burning the product. Thus, these devices must be monitored to ensure the herbal product is not burned. In addition, the vapors are first collected in the globe and then inhaled resulting in a stale inhalation in contrast to a fresh inhalation derived from inhaling air directly through the product as it is instantly vaporized from the vapor containing chamber. Such devices have proven largely unsatisfactory in the marketplace.

A variation over the globe-type vaporizer incorporates a wooden box surrounding a heating element which projects vertically or at an upwardly projecting angle. Such device typically incorporates additional unnecessary electrical circuitry on the same circuit as the heating element and presents several drawbacks. First, the wooden housing is susceptible to burning. The selection of wood also requires that the heating element is exposed and placed relatively far from the side walls of the unit creating an unnecessarily large and indiscreet unit. In other words, concealment of the heating element is not facilitated. The relatively high electrical power requirements of the other electrical components such as a variable power control switch introduces additional more complicated circuitry and also draws power from the heating element which could otherwise be used to heat the heating element thereby increasing the overall heating time.

Furthermore, such device incorporates a heating element projecting vertically from the base of the unit or at an upwardly angled orientation. Thus, during use of the vaporizing unit, the user must tilt the opening of a handpiece packed with the desired herb downwardly to engage the heating element. In this orientation, some of the loosely packed herb falls into the heating element creating smoke and losing some of the herbal product as well. Often the herb is wetted in an attempt to prevent the herb from falling out although this is not always desirable.

What is needed and heretofore unavailable is an apparatus that overcomes these and other drawbacks by providing an economical device enabling the user to avoid burning and or losing undesirable amounts of the ingredient, to improve heating time, and to allow for a closely configured compartment within which the heating element may be housed.

SUMMARY OF THE INVENTION

In accordance with a preferred embodiment of the present invention, an apparatus for vaporizing an herbal sample is provided in the form of a housing forming a heat generating compartment with an access opening. Such housing is constructed with a bottom support structure for positioning the housing on a substantially planar support surface. Within the compartment a support element is coupled to the first end of at least one heating element such that the second end of the heating element is proximate the access opening and further positioned at a height equal to or less than the height between the first end and the planar support surface. To energize the heating element a connector is provided to place the heating element in electrical communication with a power source whereby the herbal sample may be placed in close proximity with the second end of said heating element to vaporize said herbal sample after power is supplied to the heating element.

Yet another feature of the present invention is the inclusion of a heat exchanging handpiece with a heat transfer chamber having an open end for placing near the second end of the heating element and a vapor collection chamber with an end region defining an aperture wherein a user may inhale therethrough.

In one embodiment, such handpiece may further include an extension for telescopical receipt over the heating element or an insulator encircling the heating element.

Another feature of the present invention is the inclusion of an aromatic oil receiver for receiving oils that may be vaporized directly off the housing when the heating element is supplied with power.

A method of using such housing and handpiece to prevent the undesirable spillage of the herbal samples is also described herein.

BRIEF DESCRIPTION OF THE DRAWINGS

FIG. 5 is a partially broken view, in enlarged scale, of a handpiece being used in conjunction with the embodiment illustrated in FIG. 1;

FIG. 6 is a partial broken view, in enlarged scale, of an alternative handpiece being used with the embodiment of the herbal vaporizer illustrated in FIG. 1;

FIG. 7 is a partial broken view, in enlarged scale, of an alternative attachment for use with the embodiment of the herbal vaporizer illustrated in FIG. 1.

Numerous advantages and aspects of the invention will be apparent to those skilled in the art upon consideration of the following detailed description taken in conjunction with the drawings which generally provide illustrations of the invention in its presently preferred embodiments.

DESCRIPTION OF THE PREFERRED EMBODIMENTS

Figure 1:
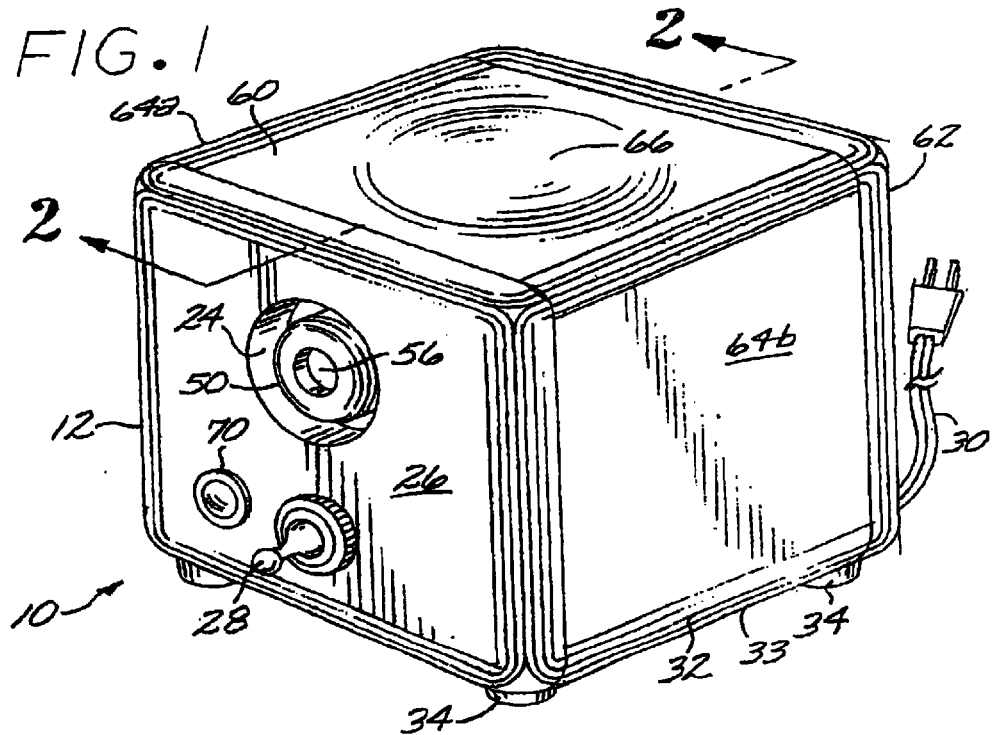
FIG. 1 is front perspective view of an herbal vaporizer embodying the present invention.
Figure 2:
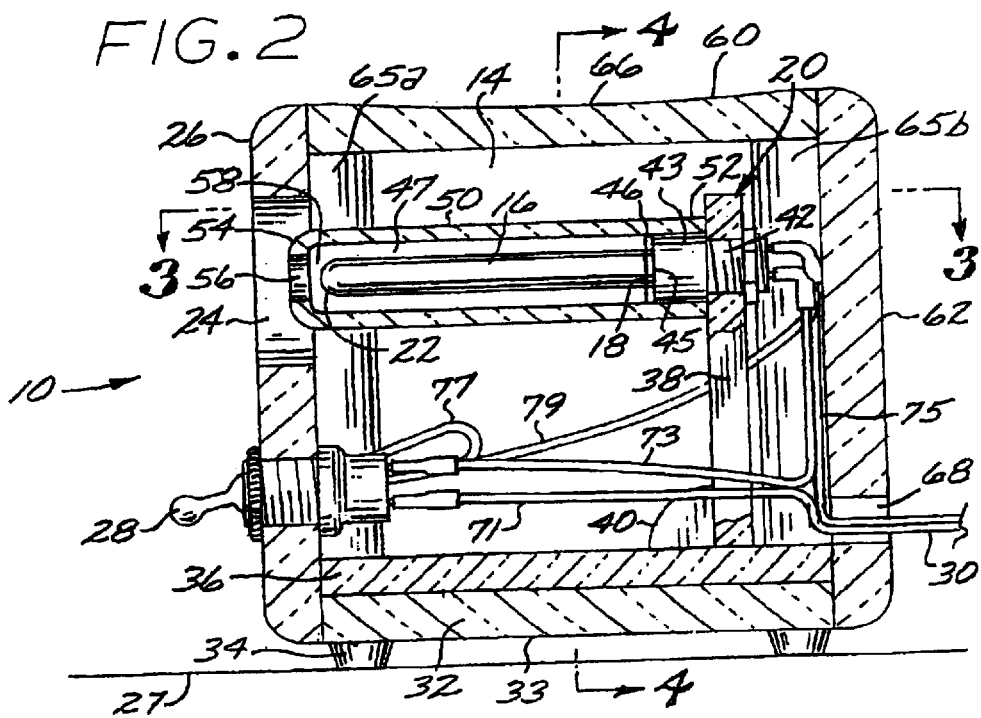
FIG. 2 is a lateral cross-sectional view, in enlarged scale, taken along lines 2—2 of FIG. 1.

Referring now to FIGS. 1–2, an herbal vaporizer, generally designated 10, is provided for extracting the active ingredients from a naturally occurring substance for remedial purposes or otherwise. In general terms, such vaporizer 10 includes a housing 12 forming a heat generating compartment 14 wherein a heating element 16 having a first end 18 is mounted to a support structure 20 to dispose the second end 22 of the heating element proximate an access opening 24 in the front wall 26 of the housing. The support structure further positions the second end of the heating element at a height equal to or lower than the first end of the heating element in relation to an underlying support surface 27. A switch 28 may be used to complete an electrical circuit between the heating element and a connector 30 which may be connected to a power source (not shown) to supply power to the heating element.

With continued reference to FIGS. 1 and 2, the generally cube-shaped housing 12 includes a bottom support 32 having a planar base mounting section 33 from which four legs 34 depend. The legs 34 are attached to the base mounting section 33 near each of the four corners of the vaporizer 10 with a suitable fastener such as a nail, screw, or adhesive. The legs serve to set the vaporizer in an upright position with the base slightly raised off the underlying support surface 27 to prevent heat generated by the heating element 16 from damaging the underlying support surface.

Resting atop the bottom support 32 is the support bracket 20 comprised of a base board 36 and an upright support 38 secured together at a right angle by a quarter round 40 spanning the width of the upright and which is adhered to or otherwise suitably fastened to both the base board and the upright. Within the upper portion of the upright is an aperture for receiving a cylindrical isolation collar 42. The isolation collar is formed of a heat resistant plastic and forms an outwardly projecting mounting post 43 forming an end mounting surface 45 with three equidistantly spaced threaded holes (not shown) for securing the heating element 16 to the upright 38 by an enlarged diameter mounting plate 46 on the first end 18 of the heating element. The enlarged diameter mounting plate 46 includes three holes (not shown) which are aligned with the three holes in the collar to receive threaded fasteners (not shown) or other suitable fasteners to secure the mounting plate to the collar. With this construction, the heating element is spaced away from the upright 38 which is typically made from wood or other suitable material. It will be appreciated that the heating element could be mounted directly to the upright or the housing if a heat resistant material is selected at the attachment surface.

In the preferred embodiment, the heating element 16 projects at a right angle to the upright to dispose its second end 22 at the same height from the underlying support surface 27 as the first end 18. In other words, the heating element is preferably disposed in a parallel relationship to a plane passing through the underlying horizontally projecting surface 27. The distal end 22 of the heating element 16 is placed in close proximity with the access opening 24 and may be positioned to terminate within the heat generating compartment 14, within the access opening 24, or just beyond the outermost surface of the front wall 26 depending on the desired concealment and accessibility of the tip 22 of the heating element 16.

Further mounted on the collar 42 is a generally hollow, cylindrically-shaped insulating sleeve 50 to be mounted on the collar in concentric alignment with the heating element 16. The insulator is spaced away from the elongated portion of the heating element forming an air insulating gap 47. The insulating sleeve 50 includes an enlarged proximal open end 52 for sliding over and nesting against the mounting post 43 of the collar. The sleeve is typically removably mounted over the heating element to facilitate replacement of the heating element if necessary. The distal end 54 of the insulating sleeve includes an aperture 56 disposed distally to the second end 22 of the heating element forming a slight clearance gap 58. The aperture is reduced in diameter relative to the diameter of the open end 52. The sleeve is preferably constructed of transparent, heat resistant, glass material.

In addition to the front wall 26 and bottom support 32, further completing the cube-shaped housing 12 to form the heat generating compartment 14 is a top wall 60 opposing the bottom support, a rear wall 62 and two opposing sidewalls 64a, 64b. Each of these walls includes a planar outer surface. Where each of the walls meet, a section of a quarter round 65a, 65b, 65c, 65d provides additional support for the respective wall joints. The top surface includes a shallow depression 66 for adding oils or other aromatic substances. As the preferred housing material is fire resistant such as stone, ceramic, tile, clay, heat resistant plastic, or other suitable fire resistant material, but may still conduct heat, such oils may be added directly into the depression to be vaporized by the heat generated in the heat generating compartment 14 and transferred through the top wall 60 to the oil. If the depression is not to be used, additional heat resistance may be provided by attaching an optional heat shield (not shown) to the interior surface of the top wall 60.

Figure 3:
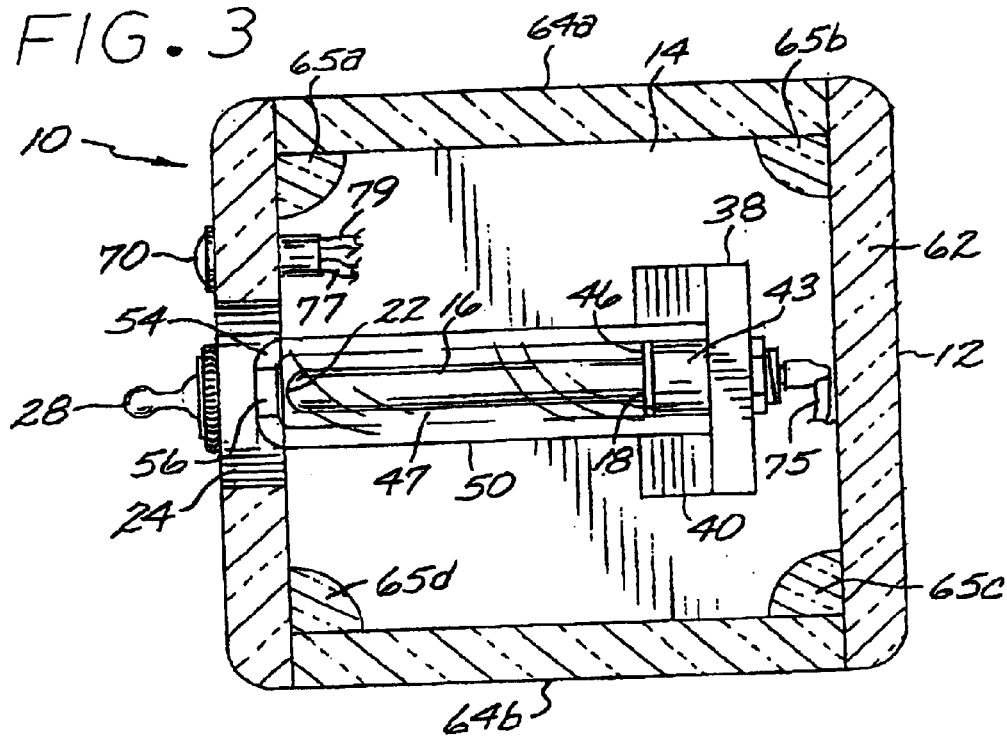
FIG. 3 is a cross-sectional view, in enlarged scale, taken along lines 3—3 of FIG. 2.

Referring now to FIGS. 1–3, the front wall 26 forms a control panel for the herbal vaporizer. Set within the front wall is a toggle switch 28 for activating the heating element 16. A power indicator light 70 is located next to the toggle switch at the lower region of the front wall 26. The rear wall of the vaporizing unit 10 includes a power source access aperture 68 for channeling the electrical cord 30, which is connected to the heating element 16, toggle switch 28, and power indicator light 70 forming an electronic circuit. As both the power indicator light and heating element are wired on the same circuit to simplify the connection, it is preferred to use a low voltage lamp to divert as little power from the heating element as possible. In addition, the use of a conventional two-position switch removes the need for more complicated circuitry associated with variable power control. Such a relatively uncomplicated circuit ensures that substantially all power is directed to the heating element thereby reducing the overall time required to heat the element to the required temperature. As the light is merely an indicator that power has been supplied to the heating element for safety purposes, it is preferable to select a lamp with minimal power requirements. Alternatively, the switch could be labeled with "on" and "off" positions to omit the light indicator altogether. To simplify the circuit even further, the switch could be also omitted with the connector 30 connected directly to the heating element 16 so the heating element is the only load on the circuit.

Figure 4:
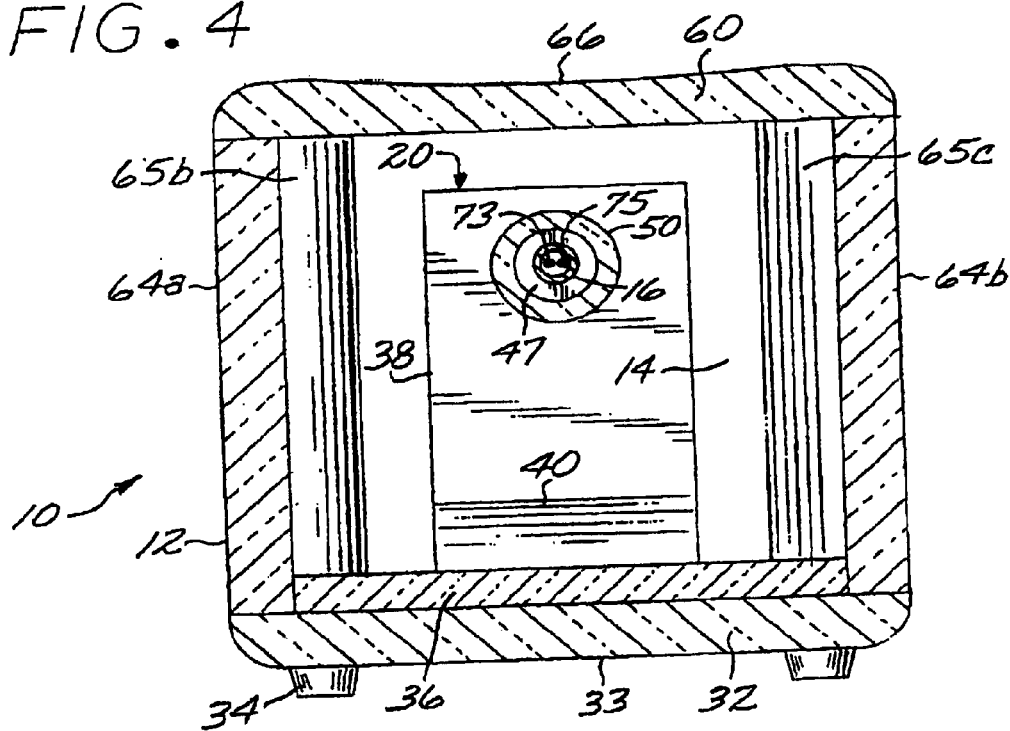
FIG. 4 is a cross-sectional view, in enlarged scale, taken along lines 4—4 of FIG. 2.

The herbal vaporizer 10 incorporates a simple electrical circuit wherein power from a power source (not shown) is routed from the connector 30 to the switch 28 via connecting wire 71 to the heating element 16 via connector wires 73 and 75. Electrical wires 73 and 75 connect to the core of the heating element which generates heat upon the application of electrical current flow (FIG. 4). The power indicator 70 is connected to the toggle switch and heating element via connector wires 77 and 79 respectively. The switch is preferably a conventional two-position toggle switch for opening and closing the circuit. When the connector 30 is plugged into a conventional power source and the switch is in the "off" position, no power is supplied to the heating element 16 and the power indicator 70 does not illuminate. When the power is supplied to the herbal vaporizer 10 and the toggle switch 28 is in the "on" position, power is supplied to the heating element 16 which begins to heat to a predetermined temperature sufficient to vaporize the herbal sample when it is placed in close proximity thereto such as in a position abutting the sleeve end 54 or relatively near the access opening 24. The power indicator 70 also illuminates to indicate the heating element is on for safety reasons. In addition, the housing conceals all but the distal tip 22 of the heating element to further protect the user from inadvertent injuries or damage. It will also be appreciated that a battery unit may be used as an alternative power source to introduce convenient portability into the herbal vaporizer 10. An alternative toggle switch and lamp combination in one device could also be incorporated using a conventional construction.

Referring now to FIG. 5, to reap the benefits of the herbal vaporizer 10, a heat exchange device also referred to as the handpiece and generally designated 72 is used. The handpiece 72 is divided into a cylindrical heat exchange chamber 74 and a truncated conical vapor collection chamber 78 separated by a filter 76 secured in an enlarged section of the handpiece which forms an exterior circular ridge. The heat exchange chamber includes a first open end 79 surrounded by a peripherally formed, enlarged lip and which is dimensioned to contain a sufficient amount of the selected herbal sample 82 which is typically cut up and packed into the heat exchange chamber. The filter 76 provides a convenient resistant wall for packing the herbal sample against and prevents unwanted particulate from entering the vapor collection chamber 78. The elongated vapor collection chamber 78 is bordered on one end with the filter 76 and includes an opposing open neck extension 80 through which a user may inhale therethrough. Conveniently a flexible extension hose 84 includes an open end 83 which may be slip fit over the outer diameter of the neck extension 80 and frictionally retained thereto to allow the user to use the vaporizer 10 from further away. The distal end 85 of the hose is used to inhale through to draw the vapor from the vapor collection chamber 78 and into the user's mouth, throat and lungs. Such handpiece 72 is preferably formed of clear glass or other heat resistant transparent material so that the user can see the vapor collect in the collection chamber 78 and is available from Hot Box Vapors in Costa Mesa, Calif.

The operation of the herbal vaporizer 10 with the first handpiece embodiment 72 will now be described. Referring now to FIGS. 1–2 and 5, the user places the herbal vaporizer 10 on a convenient support surface 27 in an upright position such that the heating element 16 is oriented in a substantially parallel alignment with the support surface. The connector 30 is plugged into a convenient wall outlet. The switch 28 is toggled to the "on" position which is indicated by illumination of the power indicator 70. Once the circuit is completed by the switch and current flows through wires 73 and 75, the heating element 16 begins to heat up. It will be appreciated that the selection of a relatively low wattage bulb for the power indicator creates a relatively minor load on the circuit resulting in most of the energy being directed to the heating element 16. This feature reduces the overall heating time. It has been found that a satisfactory heating temperature is reached in about one minute using a heating element from a conventional soldering gun. The insulating sleeve 50 traps most of the heated air and channels it toward the aperture 56 at its distal end 54 where it can be withdrawn through the aperture 56 with a relatively slight vacuum pressure.

At any time, the user may prepare the handpiece 72 by cutting up a desired amount of herbs or botanicals and packing an herbal sampling 82 into the heat exchange chamber 74 against the filter 76. The filter is sized to prevent undesirable particulate of the herbal sample 82 from being withdrawn into the vapor collection chamber 78. It is convenient to use the distal end 85 of the flexible extension hose 84 to pack the herb into the heat exchange chamber 74 using a plunger type action. Once the herbal sample has been prepared and packed and the heating element 16 warms up to a sufficient temperature, the user gains favorable purchase of the handpiece 72 and places it up against the sleeve 50 to align a central axis of the open end 79 of the handpiece 72 with the central axis of the aperture 56 of the glass insulating sleeve 50 as illustrated in FIG. 5. It will be appreciated that such arrangement with the heating element projecting parallel to the underlying surface 27 prevents the herbal sample from falling out of the heat exchange chamber onto the underlying surface or onto the heating element 16 where it may burn adding undesirable smoke particulate to the surrounding environment and create unpleasant odors.

With continued reference to FIG. 5, once the open end 79 of the handpiece 72 is aligned with the sleeve 50, the user inhales through the distal end 85 of the tube 84 creating a vacuum in the tube and adjacent handpiece 72 to draw the heated air from between the sleeve 50 and heating element 16 out through the aperture 56 and into the heat exchange chamber 74. Once the drawn hot air reaches the herbal sample 82, the sample begins to vaporize and the desired vapors are drawn through the filter 76 into the vapor collection chamber 78 through further inhalation. The filter prevents any undesirable larger particles from also entering the chamber 78. Through controlled breathing, the user can control the amount of vapor entering the chamber 78 prior to inhaling the collected vapors. The process may be repeated as necessary until the herbal sample 82 is used up. It is then a simple matter to repack the heat exchange chamber 74 with additional herbal sample 82 and restart the vapor production, collection, and inhalation process. Once the user is finished, the switch 28 is moved to the "off" position and the power indicator enters an unlit state indicating the herbal vaporizer 10 is powered off.

As illustrated in FIG. 6 wherein like components are numbered alike, a modified hollow handpiece 90 is also contemplated for use with the vaporizer 10. Such handpiece 90 includes a modified heat transfer chamber 92 having an enlarged open end 94 with extension 96 wherein a select quantity of the desired herb 82 is placed. The extension is formed with a smaller diameter than the access opening 24 and a slightly larger diameter than the insulating sleeve 50 such that the extension slip fits over the sleeve 50. The length of the extension is sufficient to releasably retain the modified handpiece 90 to the insulating sleeve without being held in place by the user. When in place, the central axis of the extension is aligned with the central axis of the sleeve 50. Such modified handpiece frees the user from having to hold the handpiece close to the insulating sleeve during use. Thus, the sleeve 50 provides a convenient mounting region for mounting the handpiece 90 to the heating element 16. Alternatively, the extension 96 could be sized to fit snugly against the inner diameter of the access opening 24 to releasably retain the handpiece 90 to the housing with the herbal sample 82 in close proximity to the heating element 16 or insulator 50. The modified handpiece 90 is also available from Hot Box Vapors in Costa Mesa, Calif.

At the opposite end of the heat transfer chamber 92 is the filter or screen 76 preventing the herb from being withdrawn from the heat transfer chamber during inhalation. The filter also separates the heat exchange chamber 92 from the vapor collection chamber 78. The construction of the filter 76, vapor collection chamber 78, and extension hose 84 is the same as the construction for the like components described above in relation to the first embodiment handpiece 72.

The use of the herbal vaporizer with the modified handpiece 90 is similar to the use with the handpiece 72. The only differences are that after the herbal sample 82 is packed into the heat exchange chamber 92, the user gains favorable purchase of the handpiece and slides the extension 96 between the access opening 24 and sleeve 50 to mount the handpiece 90 thereon. When mounted, the central axis of the heat exchange chamber 92 is aligned with the central axis of the sleeve (FIG. 6). The user is then free to remove his or her hand from the handpiece 90. Production and collection of the vapor is created by inhaling through the hose 84 as described above following application of power to the heating element 16. When the user desires to repack the heat exchange chamber 92, the user grasps the handpiece 90 and slides it off of the sleeve 50 to expose the open end 94 of the modified handpiece 90. The inner diameter of the access opening 24 acts as a rough guide for the extension 96 when being installed or removed.

Figure 8:
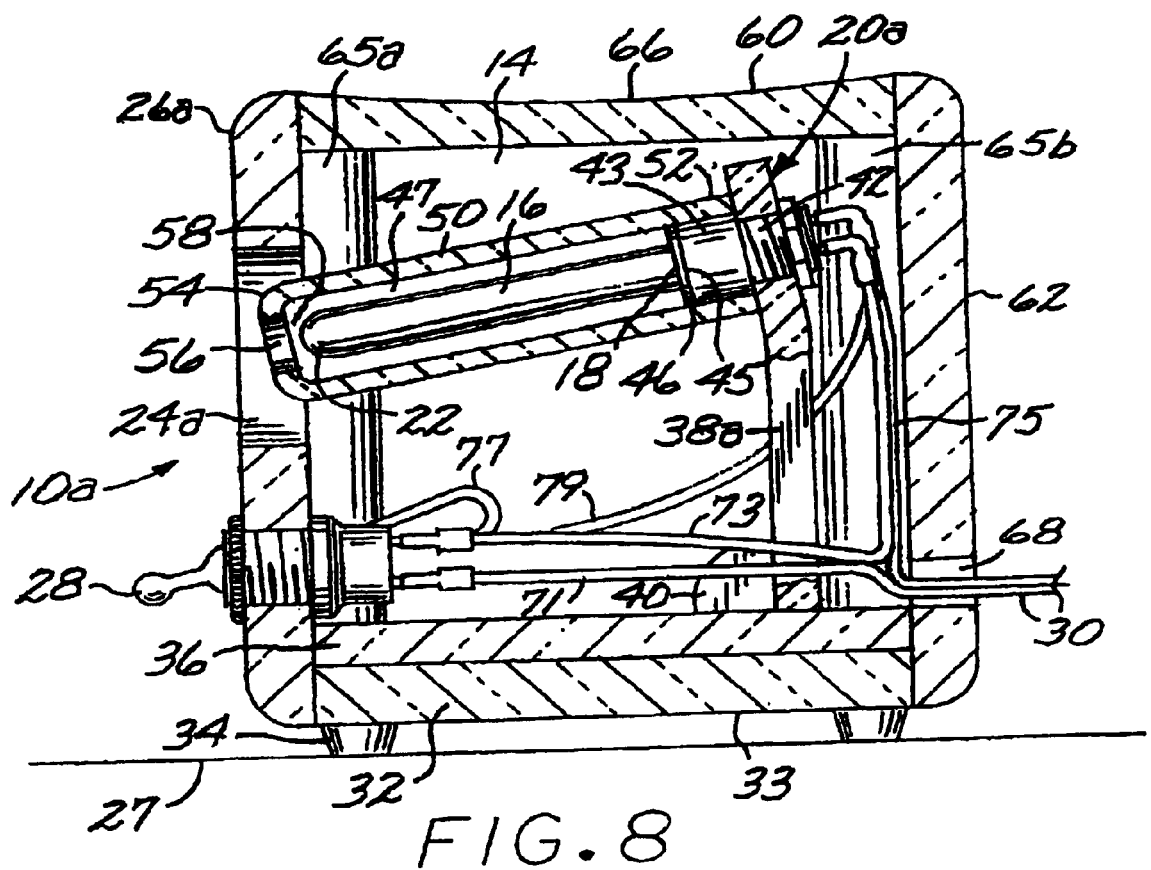
FIG. 8 is a similar view as in FIG. 2 of an alternative embodiment with a downwardly projecting heating element.

It will be appreciated that the positioning of the second end 22 of the heating element 16 relative to the first end 18 of the heating element with respect to the underlying support surface 27 or base 32 of the herbal vaporizing unit 10 ensures that the handpiece opening in either embodiment is not tilted downwardly at any time thus preventing inadvertent spillage of the herbal sample 82 from the heat exchange chamber 74. In other words, the second end 22 of the heating element projects either parallel to or at downward angle, including straight down, from the first end 18 of the heating element 16. The heating element 16 could angle downwardly or the support structure 20 may be constructed to accommodate the downward angling of the heating element 16. Alternative vaporizer embodiment 10a in FIG. 8, wherein like parts are numbered alike, depicts such an arrangement with the upright member 38a of the support structure 20a angled to lower the second end 22 of the heating element 16 proximate the opening 24a in the front wall 26a.

As described above, the herbal vaporizer is also constructed to vaporize aromatic oils. In one embodiment, the oil or oil and water mixture is placed into the shallow depression 66 on the top wall 60 of the vaporizer 10 (FIG. 1). The user then connects the connector 30 to the power source to begin heating the heating element 16 by selecting the "on" position for the toggle switch 78. Hot air from the heating element fills the heat generating compartment 14. The relatively small access opening 24 substantially inhibits the ambient air from mixing with heated air in the compartment 14. Once the hot air reaches a given temperature and transfers this heat energy through the top surface 60 to the depression 66 and oil therein, the oil begins to vaporize adding the desired scent to the surrounding environment. Additional oil or oil and water mixtures are added as desired.

Referring now to FIG. 7 wherein like components are numbered alike, aromatic oils may alternatively be vaporized using an oil vaporizing attachment, generally designated 100, which includes a cylindrical extension 102 for a slip fit releasable coupling to the insulating sleeve 50 in a similar manner and construction as the extension 96 described above in relation to the modified handpiece 90. The cylindrical extension tapers to an outwardly extending, narrow neck portion which turns upwardly to terminate in a stand 114. Positioned on the stand is a fluid receptacle 104 with a bowl section 106 for receiving relatively small quantities of aromatic oils 108 or oil mixed with water. The bowl is open at the top 110 allowing the vaporized oil to escape into the surrounding area when heated. Conveniently, a handle 116 is provided for removing the fluid receptacle 104 from the stand 114. A hollow passageway 112 in the neck and stand allows heated air from the heating element 16 to access the bottom of the bowl 106 to heat the fluid 108 therein. The construction of the attachment is such that the bowl is positioned sufficiently close to the heating element to vaporize the oil contained in the bowl. It is contemplated that the fluid receptacle 104 may be detachable from the stand 114 or may be formed as an integral unit. Such fluid receptacle and the stand with attachment are available from Hot Box Vapors in Costa Mesa, Calif.

To operate, the user attaches the oil vaporizing attachment 100 to the sleeve 50 by slip fitting the exterior 102 between the access opening 24 and outside diameter of the sleeve 50. The bowl 106 may either abut the distal tip 54 of the sleeve or be placed in close proximity thereto. The extension 102 may be slid along a portion of the sleeve 50 to achieve preferred vaporization rates. The user then adds the desired amount of aromatic solution 108 into the bowl 106. The connector 30 is then plugged into the power source and the switch 28 is switched "on" to energize the heating element 16. As the heating element 16 increases in temperature, the heat is transferred through the sleeve 50 and out the aperture 56 to the wall of the bowl 106. Such heat is then transferred to the oil 108 in the bowl which vaporizes and escapes through the open top 110 to the surrounding environment. The power indicator 10 (FIG. 1) serves as a reminder to turn the switch to the "off" position when the oil is used up.

While several forms of the present invention have been illustrated and described, it will also be apparent that various modifications may be made without departing from the spirit and scope of the invention.

What is claimed is:

1. An herbal vaporizing kit assembly comprising:

a fire-resistant housing forming a heat generating compartment having an access opening formed in a side wall thereof, said housing being constructed with a bottom support structure for positioning said housing on a substantially planar support surface;

at least one elongated heating element having a first end and a second end;

a support element in said compartment coupled to said first end to position said second end proximate said access opening, said support element further positioning said second end at a height equal to or less than the height between the first end and said planar support surface;

an elongated insulating sleeve mounted to said support element in a concentric relationship with said heating element, said sleeve including an aperture proximate said second end;

a connector in electrical communication with said heating element and constructed to be placed in electrical communication with a power source;

an actuator electrically coupled to said connector for energizing said heating element upon connection of said connector to said power source;

a heat exchanging transparent handpiece including a heat transfer chamber with an open end for abutting said second end of said heating element, a filter at an opposing end of said heat transfer chamber, and a vapor collection chamber with an end region defining an aperture wherein a user may inhale therethrough; and an elongated flexible extension tube having a first end for connection to said end region and a distal end for inhalation therethrough whereby said heat transfer chamber may be packed with said herbal sample and placed in close proximity with said second end and a user may inhale through said distal end to vaporize said herbal sample and draw said vapor into said vapor collection chamber for subsequent inhalation.

2. An apparatus for extracting live ingredients by vaporizing an herbal sample through the application of heat comprising:

a fire-resistant housing forming a heat generating compartment having a lower planar surface, said housing including an access opening defining a central axis oriented at a right angle to said planar surface;

an elongated heating element recessed at least partially within said compartment and having a first end for mounting said heating element and a second end for placement proximate said access opening;

a support structure including a heat resistant mounting collar coupled to said first end of said heating element for isolating said heating element from said housing and positioning said second end of said heating element proximate said access opening;

an insulating element extending from said support structure in a radially exterior concentric relationship with said heating element and including an opening proximate said second end of said heating element;

an actuator electrically coupled to said heating element for activation thereof;

a power indicator providing an indication of the application of power when said actuator is actuated to a first position; and a heat exchanging element forming an ingredient chamber including a first opening at one end for abutting said insulating element opening and further including a second opening having a filter connected to a vapor collection chamber, said vapor collection chamber including an opposing end for inhalation therethrough.

3. An apparatus for extracting active ingredients by vaporizing an herbal sample through the application of heat comprising:

a fire-resistant housing forming a heat generating compartment having a lower planar surface, said housing including an access opening;

an elongated heating element recessed at least partially within said compartment and having a first end for mounting said heating element and a second end for placement proximate said access opening;

a support structure including a heat resistant mounting collar coupled to said first end of said heating element for isolating said heating element from said housing and positioning said second end of said heating element in a radially downwardly projecting direction from said first end and proximate said access opening;

an insulating element extending from said support structure in a radially exterior concentric relationship with said heating element and including an opening proximate said second end of said heating element;

an actuator electrically coupled to said heating element for activation thereof; and a heat exchanging element forming an ingredient chamber including a first opening at one end for abutting said insulating element opening and further including a second opening having a filter connected to a vapor collection chamber, said vapor collection chamber including an opposing end for inhalation therethrough.

4. An apparatus for extracting active ingredients from an herbal sample through vaporization comprising:

a housing forming a heat generating compartment having an access opening formed in a side wall thereof, said housing being constructed with a bottom support structure for positioning said housing on a substantially planar support surface;

at least one elongated heating element having a first end and a second end;

a support element in said compartment coupled to said first end to position said second end proximate said access opening, said support element further positioning said second end at a height equal to or less than the height between the first end and said planar support surface;

a connector in electrical communication with said heating element and constructed to be placed in electrical communication with a power source whereby, upon connection of said connector to said power source, said herbal sample may be placed in close proximity with said second end of said heating element to vaporize said herbal sample; and an elongated insulator with a first end mounted to said support element to dispose said insulator in an enlarged circumferential relationship with said heating element, said insulator including an aperture in close proximity with said second end.

5. The apparatus as set forth in claim 4 further including:

a heat exchanging transparent handpiece including a heat transfer chamber with an open end for placement in close proximity with said second end of said heating element, a filter at an opposing end of said heat transfer chamber, and a vapor collection chamber with an end region defining an aperture wherein a user may inhale therethrough; and whereby said heat transfer chamber may be packed with said herbal sample and placed in close proximity with said second end and a user may inhale through such aperture to vaporize said herbal sample and draw said vapor into said vapor collection chamber for subsequent inhalation.

6. The apparatus as set forth in claim 4 further including:

an elongated flexible extension tube having a first end for connection to said end region and a distal end for inhalation therethrough.

7. The apparatus as set forth in claim 4 wherein:

said support element isolates said heating element from said housing sides.

8. The apparatus set forth in claim 4 wherein:

said housing is in the form of a cube.

9. The apparatus as set forth in claim 4 further including:

a heat exchanging handpiece including a heat transfer chamber with an open end including region including an extension forming a mounting region to be telescopically received over a portion of said insulator and interior to an inside diameter of said access opening, said handpiece further including a filter at an opposing end of said heat transfer chamber, and a vapor collection chamber with an end region defining an aperture wherein a user may inhale therethrough; and whereby said heat transfer chamber may be packed with said herbal sample and placed in close proximity with said second end and a user may inhale through said aperture to vaporize said herbal sample and draw said vapor into said vapor collection chamber for subsequent inhalation.

10. The apparatus as set forth in claim 4 wherein:

said housing is constructed from a material selected from the group consisting of ceramic, stone, clay, or heat resistant plastic.

11. The apparatus as set forth in claim 4 wherein:

said housing includes a top surface with a shallow depression for receipt of an aromatic oil, said oil being vaporized by the heat generated from said heating element.

12. The apparatus as set forth in claim 4 wherein:

said housing includes six side walls with a support adjoining each adjacent side wall.

13. The apparatus as set forth in claim 4 wherein:

said heating element is fully recessed within said heat generating compartment.

14. The apparatus as set forth in claim 4 further including:

a heat resistant isolation collar mounted between said heating element and said support element.

15. The apparatus as set forth in claim 4 further including:

an actuator in electrical communication with said connector and said heating element for energizing said heating element upon the connection of the connector to a power source.

16. The apparatus as set forth in claim 4 further including:

an attachment having a liquid receiving bowl with an extension for coupling said bowl to said insulator in close proximity to said second end of said heating element.

\* \* \* \* \*